(12) United States Patent
Laudo

(10) Patent No.: US 7,499,167 B2
(45) Date of Patent: Mar. 3, 2009

(54) AEROSOL TRIGGER DEVICE AND METHODS OF DETECTING PARTICULATES OF INTEREST USING AN AEROSOL TRIGGER DEVICE

(75) Inventor: John S. Laudo, Hilliard, OH (US)

(73) Assignee: Battelle Memorial Institute, Columbus, OH (US)

( * ) Notice: Subject to any disclaimer, the term of this patent is extended or adjusted under 35 U.S.C. 154(b) by 214 days.

(21) Appl. No.: 11/486,946

(22) Filed: Jul. 14, 2006

(65) Prior Publication Data
US 2009/0027674 A1    Jan. 29, 2009

Related U.S. Application Data

(60) Provisional application No. 60/699,056, filed on Jul. 14, 2005.

(51) Int. Cl.
    *G01N 21/25* (2006.01)
(52) U.S. Cl. ..................................... 356/417
(58) Field of Classification Search .................. 356/417
    See application file for complete search history.

(56) References Cited

U.S. PATENT DOCUMENTS

| | | | |
|---|---|---|---|
| 2,721,495 A | | 10/1955 | Schaefer |
| 3,759,617 A | * | 9/1973 | Barringer ..................... 356/36 |
| 4,255,172 A | | 3/1981 | Smith |
| 4,868,398 A | | 9/1989 | Mulcey et al. |
| 4,942,297 A | | 7/1990 | Johnson et al. |
| 5,397,536 A | * | 3/1995 | Nakano et al. ................ 422/86 |
| 5,498,271 A | | 3/1996 | Marple et al. |
| 5,701,012 A | | 12/1997 | Ho |
| 5,717,147 A | | 2/1998 | Basch et al. |
| 5,866,430 A | | 2/1999 | Grow |

(Continued)

FOREIGN PATENT DOCUMENTS

EP    0 421 156 A2    4/1991

(Continued)

OTHER PUBLICATIONS

Gard, E., Mayer, J.E., Morrical, B.D., Dienes, T. Fergeson, D.P., and Prather, K.A.; "Real-Time Analysis of Individual Atmospheric Aerosol Particles: Design and Performance of a Portable ATOFMS," Anal. Chem., 1997, 69, 4083-4091.

(Continued)

*Primary Examiner*—Kara E Geisel
(74) *Attorney, Agent, or Firm*—Stevens & Showalter, LLP

(57) ABSTRACT

A trigger device for detecting particles of interest comprises a sample substrate, a collector, a read head and a processor. The collector is positioned proximate to at least a portion of a first side of a sample substrate and is operated to deposit a sample on the substrate within a sample area. The read head is positioned proximate to the sample area on a second side of the sample substrate generally opposite the collector and comprises a concave reflection surface having a back side positioned proximate to the sample area so as to register the substrate within the sample area with the read head. The processor is operatively configured to analyze a signal from one or more detectors of the read head and to trigger an event if particulates of interest are detected in the sample.

35 Claims, 9 Drawing Sheets

U.S. PATENT DOCUMENTS

| | | | |
|---|---|---|---|
| 5,880,830 | A * | 3/1999 | Schechter .................. 356/318 |
| 5,895,922 | A | 4/1999 | Ho |
| 5,989,824 | A | 11/1999 | Birmingham et al. |
| 6,010,554 | A | 1/2000 | Birmingham et al. |
| 6,040,191 | A | 3/2000 | Grow |
| 6,062,392 | A | 5/2000 | Birmingham et al. |
| 6,110,247 | A | 8/2000 | Birmingham et al. |
| 6,267,016 | B1 | 7/2001 | Call et al. |
| 6,363,800 | B1 | 4/2002 | Call et al. |
| 6,386,015 | B1 | 5/2002 | Rader et al. |
| 6,435,043 | B1 | 8/2002 | Ferguson et al. |
| 6,483,581 | B1 | 11/2002 | Ben-Amotz et al. |
| 6,506,345 | B1 | 1/2003 | Lee et al. |
| 6,510,727 | B2 | 1/2003 | Reiter et al. |
| 6,695,146 | B2 | 2/2004 | Call et al. |
| 6,698,592 | B2 | 3/2004 | Kenning et al. |
| 6,707,548 | B2 | 3/2004 | Kreimer et al. |
| 6,717,668 | B2 | 4/2004 | Treado et al. |
| 6,729,196 | B2 | 5/2004 | Moler et al. |
| 6,732,569 | B2 | 5/2004 | Ondov et al. |
| 6,734,962 | B2 | 5/2004 | Treado et al. |
| 6,765,668 | B2 | 7/2004 | Gardner, Jr. et al. |
| 6,788,860 | B1 | 9/2004 | Treado et al. |
| 6,799,119 | B1 | 9/2004 | Voorhees et al. |
| 6,806,465 | B2 | 10/2004 | Anderson et al. |
| 6,841,773 | B2 | 1/2005 | McLoughlin et al. |
| 6,985,818 | B1 * | 1/2006 | Samuels ...................... 702/22 |
| 2002/0003210 | A1 | 1/2002 | Marcus |
| 2002/0030811 | A1 | 3/2002 | Schindler |
| 2002/0070148 | A1 | 6/2002 | Roberts et al. |
| 2002/0081748 | A1 | 6/2002 | Roberts et al. |
| 2002/0184969 | A1 | 12/2002 | Kodas et al. |
| 2003/0010907 | A1 | 1/2003 | Hayek et al. |
| 2003/0020768 | A1 | 1/2003 | Renn |
| 2003/0082825 | A1 | 5/2003 | Lee et al. |
| 2003/0098422 | A1 | 5/2003 | Silcott et al. |
| 2003/0221063 | A1 | 12/2003 | Hill et al. |
| 2004/0010379 | A1 | 1/2004 | Craig et al. |
| 2004/0016308 | A1 | 1/2004 | Rogers et al. |
| 2004/0027938 | A1 | 2/2004 | Craig |
| 2004/0065159 | A1 | 4/2004 | Sioutas |
| 2004/0068193 | A1 | 4/2004 | Barnes et al. |
| 2004/0118222 | A1 | 6/2004 | Cornish et al. |
| 2004/0121402 | A1 | 6/2004 | Harper et al. |
| 2004/0197493 | A1 | 10/2004 | Renn et al. |
| 2004/0222372 | A1 | 11/2004 | McLoughlin et al. |
| 2004/0227938 | A1 | 11/2004 | Craig |
| 2004/0232052 | A1 | 11/2004 | Call et al. |
| 2005/0028616 | A1 | 2/2005 | Marple et al. |
| 2005/0041774 | A1 | 2/2005 | Saitoh et al. |
| 2005/0046664 | A1 | 3/2005 | Renn |
| 2005/0070025 | A1 | 3/2005 | Mooradian et al. |
| 2005/0079349 | A1 | 4/2005 | Hampden-Smith et al. |
| 2005/0105079 | A1 | 5/2005 | Pletcher et al. |

FOREIGN PATENT DOCUMENTS

| | | |
|---|---|---|
| WO | WO 93/07471 A | 4/1993 |
| WO | WO 96/29925 A2 | 10/1996 |
| WO | WO 03/036273 A1 | 5/2003 |
| WO | WO 2006/001852 A2 | 1/2006 |
| WO | WO 2006/091221 A2 | 8/2006 |

OTHER PUBLICATIONS

Hansen, A.D.A., Rosen H., and Novakov, T.; "The aethalometer—an instrument for the real-time measrement of optical absorption by aerosol particles," Sci. Total Environ., 1984, 36, 191.

Jayne, J.T., Leard, D.C., Zhang, X., Davidovits, P. Smith, K.A. Kolb, C.E., Worsnop, D.R..; "Development of an Aerosol Mass Spectrometer for Size and Composition Analysis of Submicron Particles," Aerosol Sci. Tech., 2000, 34, 49-70.

McCreery R.L., Raman Spectroscopy for Chemical Analysis, Chemical Analysis, vol. 157, 2000.

Prather, K.A., Nordmeyer, T., Salt, K.; "Real-Time Characterization of Individual Aerosol Particles Using Time-of-Flight Mass Spectrometry," Anal. Chem., 1994, 66, 1403-1407.

Rupprecht & Patashnick, Co., Patent pending, 2001.

Rupprecht, G., Patashnick, H., Beeson, D.E., Green, R.N. and Meyer, M.B.; "A New Automated Monitor for the Measurement of Particulate Carbon in the Atmosphere," Presented at Particulate Matter: Health and Regulatory Issues, Pittsburgh, PA, Apr. 4-6, 1995.

Stolzenburg, M.R. and Hering, S.V., "Method for the Automated Measurement of Fine Particle Nitrate in the Atmosphere," Environ. Sci. Technol., 2000, 34, 907-914.

Rosch, Petra, Harz, Michaela, Peschke, Klaus-Dieter, Ronneberger, Olaf, Burkhardt, Hans, Schule, Andreas, Schmauz, Gunther, Lankers, Markus, Hofer, Stefan, Thiele, Hans, Motzkus, Hans-Walter, and Popp, Jurgen, On-Line Monitoring and Identification of Bioaerosols, Anal. Chemistry, vol. 78, No. 7, Apr. 1, 2006.

Dycor Biological Detection Products, www.dycor.com/products/biologicalDet.htm, Jun. 6, 2005.

Humphries, Allen, A Simple Guide To How Aerosol Particle Counters Work, www.pmeasuring.com/particleCounting/appNotes/aerosol/app59air/viewHtml, Apr. 18, 2005.

Patrick Wach; International Search Report and Written Opinion for PCT Application No. PCT/US2006/027368; Dec. 18, 2006; European Patent Office; Rijswijk The Netherlands.

Puk Groeneveld-Van Der Spek; International Search Report and Written Opinion for PCT Application No. PCT/US2006/027689; May 18, 2007: European Patent Office; Rijswijk The Netherlands.

Nicolas Ruchaud, Communication pursuant to Article 94(3) EPC for EPO Application No. 06 787 297.8; May 19, 2008; European Patent Office, Rijswijk The Netherlands.

* cited by examiner

AEROSOL TRIGGER DEVICE AND METHODS OF DETECTING PARTICULATES OF INTEREST USING AN AEROSOL TRIGGER DEVICE

CROSS REFERENCE TO RELATED APPLICATION

This application claims the benefit of U.S. Provisional Patent Application Ser. No. 60/699,056, filed Jul. 14, 2005 entitled "AEROSOL TRIGGER DEVICE AND METHODS OF DETECTING PARTICULATES OF INTEREST USING AN AEROSOL TRIGGER DEVICE", the disclosure of which is hereby incorporated by reference.

BACKGROUND OF THE INVENTION

The present invention relates in general to systems and methods for the separation and collection of particulates from a fluid stream and in particular, to systems and methods for the collection, detection and/or analysis of airborne particulates of interest including biological and chemical agents.

Atmospheric particulate matter has received an increasing amount of attention in recent years because of its potential impact on human health, and because of the role particles play in atmospheric transport and deposition of pollutants, and in radiative and climatic processes. For example, it may be desirable to analyze the air in a predetermined location for particulates that fall within a range of sizes that can be inhaled, such as naturally occurring or artificially produced airborne pathogens, allergens, bacteria, viruses, fungi and biological or chemical agents that are found in or are otherwise introduced into the location.

As another example, it may be desirable to detect the presence of particular airborne particulates in semiconductor clean rooms, pharmaceutical production facilities and biotechnology laboratories to verify that there has been no contamination produced in such environments that would create undesirable environmental exposures or adversely affect manufacturing, testing or experimental processes. Similarly, the ability to detect the presence of particular airborne particulates in hospitals, nursing homes, rehabilitation centers and other care facilities may be beneficial to assist in preventing the spread of disease, infection or harmful bacteria.

Air monitoring further finds application for assessments of human health risk, environmental contamination or for compliance with National Air Quality Standards (NAAQS). As yet further examples, it may be desirable to monitor the air in public and commercial building air purification and distribution systems, work sites such as mines, sewage facilities, agricultural and manufacturing facilities, outside areas such as street corners, flues and smokestacks and other locations where it is desirable to monitor environmental hygiene, such as residences exposed to microorganisms, plants or animals.

SUMMARY OF THE INVENTION

The various embodiments of the present invention provide systems and methods for identifying materials comprising particulates entrained in a gaseous fluid by separating particulates from the air or other gaseous fluid, and by collecting and concentrating a sample of the particulates in a specimen suitable for analysis.

According to an aspect of the present invention, a trigger device for detecting particles of interest comprises a sample substrate, a collector, a read head and a processor. The collector is configured to deposit samples of particulates within a sample collection area. The read head is positioned proximate to the sample collection area generally opposite of the collector and comprises a concave reflection surface having a back surface positioned proximate to the sample area so as to register the sample area with the read head. The read head further comprises an illumination source that illuminates at least a portion of the sample area and at least one detector that detects radiation within the read head including illumination reflected from the reflection surface and radiation which may be emitted by samples collected within the sample area. The processor is operatively configured to analyze a signal from the detector(s) and to trigger an event if particulates of interest are detected in the sample area.

According to another aspect of the present invention, a read head for a trigger device comprises a housing, a reflection surface, a radiation source, at least one filter and at least one detector. The housing includes a first surface having a channel therethrough for receiving a tape substrate. The reflection surface, e.g., a parabolic mirror, is correspondingly positioned adjacent to at least a portion of the channel in the first surface. The radiation source, such as an ultraviolet Light Emitting Diode, is configured to emit a beam that is directed towards the reflection surface. The beam is reflected by the reflection surface and passes through the filter(s), which are arranged to filter the beam before the beam impinges upon the detector(s). If multiple detectors are utilized, the beam may be filtered into different spectral regions where energy in each spectral region is directed to a different detector.

According to yet another aspect of the present invention, a read head for a trigger device comprises a housing including a first surface having a channel therethrough for receiving a tape substrate. A concave reflection surface is oriented such that a backside of the reflection surface is adjacent to at least a portion of the channel in the first surface so as to register with the tape substrate when the tape substrate is positioned within the channel, e.g., within a sample collection area of the read head. A radiation source is configured to emit a beam that is directed towards the reflection surface. A first detector is arranged to receive radiation that is filtered into a first spectral range and a second detector is arranged to receive radiation that is filtered into a second spectral range that is different from the first spectral range. The radiation received by the first and second detectors may comprise illumination radiation from the radiation source that is reflected from the reflection surface and/or radiation which may be emitted by samples collected within the sample collection area.

According to yet another aspect of the present invention, a method of detecting a particulate of interest is described. A collection device is enabled to deposit a sample of particulates onto a tape substrate during a collection period in a predetermined sample collection area. A read head is utilized to illuminate the sample area during at least a portion of the collection period to generate sample data, which is collected and filtered. Also, slope and threshold information is computed from the sample data to determine if an event has occurred with sufficient confidence to generate an alarm event. The tape may index to a clean substrate region after the collection period, thus enabling autonomous operation. Collecting a sample may comprise impacting particulates onto the tape in a localized spot having a diameter smaller than approximately 2 millimeters. The method may further comprise arranging the collection device and the read head so as to achieve a light tight optical system where the sample area is illuminated by the optical read head.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals, and in which.

DETAILED DESCRIPTION OF THE INVENTION

In the following detailed description of the preferred embodiments, reference is made to the accompanying drawings that form a part hereof, and in which is shown by way of illustration, and not by way of limitation, specific preferred embodiments in which the invention may be practiced. It is to be understood that other embodiments may be utilized and that changes may be made without departing from the spirit and scope of the present invention.

Figure 1:
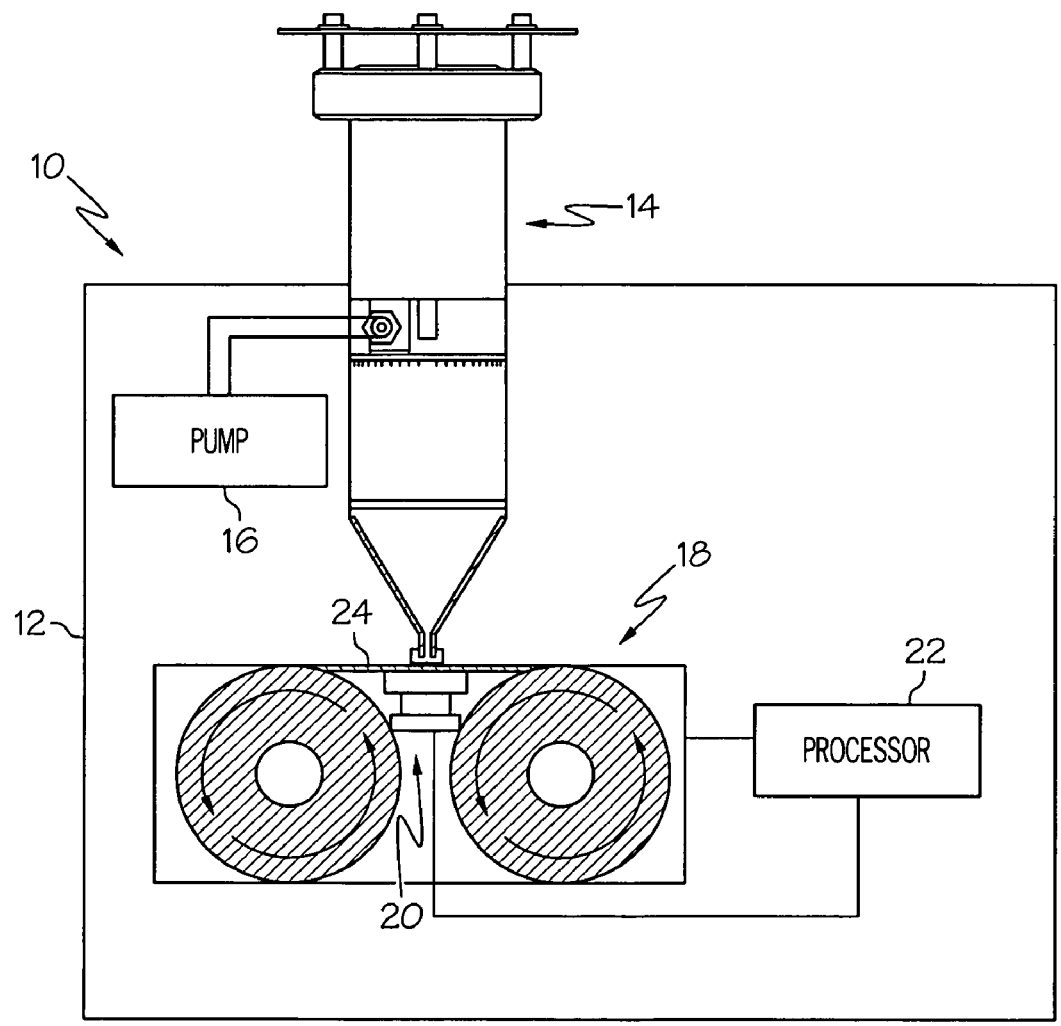
FIG. 1 is a schematic illustration of a stand-alone trigger device according to an embodiment of the present invention.

Referring now to the drawings, and particularly to FIG. 1, a stand-alone trigger device 10 for detecting particulates of interest in a fluid stream includes generally, a housing 12, a collector 14, a pump 16, a sample substrate 18, a read head 20 and a processor 22. The housing 12 and/or the relationship between the collector 14 and read head 20 with respect to the sample substrate 18 provides a substantially light tight arrangement so as to block ambient light from excessively interfering with the read head interrogation of a sample at least within a sample collection area as will be explained in greater detail herein.

The pump 16 draws and accelerates a fluid stream, such as from atmospheric aerosols, through the collector 14 towards a sample collection area. The read head 20 is positioned proximate to the sample collection area generally opposite of the collector 14 and the sample substrate 18 is oriented generally between the collector 14 and the read head 20. During operation of the collector 14, particulate matter that is entrained in the stream is extracted and deposited onto the sample substrate 18 within the relatively small, defined sample collection area and the fluid stream is evacuated up and away from the sample substrate 18.

An optional mask 24 may be provided between the collector 14 and the sample substrate 18 to prevent the particulates from depositing onto the sample substrate 18 in areas adjacent to the current sample area. During operation of the trigger device 10, the read head 20 interrogates the particulates collected within the sample area of the sample substrate 18. The processor 22 analyzes the output from the read head 20 and if particulates of interest are detected in the sample, an action event may be triggered, such as sounding an alarm, sending a message, or taking other appropriate action. A single vacuum pump 16 is illustrated in FIG. 1 for purposes of clarity. However, multiple vacuum pumps 16 and coupling arrangements may be implemented as the specific application dictates.

Solid Surface Small Area Impactor

Referring to FIGS. 2-5, the collector 14 includes an inlet 26, a pre-impactor 28, an impactor 30, a nozzle 32 and a pump coupling arrangement 34. The inlet 26 is physically connected to the pre-impactor 28 by a coupling device, such as screws 36 or other suitable securing arrangement. Covers or other devices may be provided to prevent foreign objects from entering the collector while the inlet(s) 26 are removed from the collector 14, e.g., during transportation of the stand-alone trigger device 10.

With particular reference to FIG. 5, the inlet 26, which extends outside of the housing 12, includes a cap 38, an inlet opening 40 and a generally funnel shaped first fluid passageway 42. The fluid stream enters the inlet 26 through the inlet opening 40 and is drawn through the first fluid passageway 42 into the pre-impactor 28. The cap 38 may serve as a rain plate or other environmental protection structure that prevents the collection system from ingesting large particles including rain drops etc. Moreover, the inlet opening 40 comprises substantially the entirety of the circumference of the inlet 26 as illustrated, but other opening arrangements may alternatively be implemented. Additionally, the first fluid passageway 42 may be of any shape length necessary to locate the sample collection point to a desired location. In this regard, the first fluid passageway 42 may comprise one or more intermediate structures such as extension tubes that serve to extend the distance between the inlet 26 and the pre-impactor 28.

The pre-impactor 28 includes a pre-impactor input 44, a particulate filtering arrangement 46 and a second fluid passageway 48. The fluid stream is directed through the pre-impactor input 44 via the first fluid passageway 42 to the particulate filtering arrangement 46. As shown, the particulate filtering arrangement 46 is implemented as a cup 50 that collects and holds particulates that exceed a predetermined size, e.g., particulates greater than approximately 10 μm. The filtered fluid stream is drawn out of the cup 50 and is directed along the outside of the cup 50 into the second fluid passageway 48 to the impactor 30.

The impactor 30 accelerates the fluid stream through a third fluid passageway 52 and out the nozzle 32 towards the sample substrate 18 to form a sample that is contained in a small, definable sample area. Under the above arrangement, particle impaction in the sample area is governed by the dimensionless Stokes number (Stk) according to the expression:

$$Stk = \frac{\rho_{particle} C_c d^2_{particle} V}{18 \eta_{air} d_{impactor}}$$

where:

$\rho_{particle}$ is the particle density, $C_c$ is the slip correction factor, $d^2_{particle}$ is the particle diameter, V is the velocity of the air jet out of the nozzle, $\eta_{air}$ is the air viscosity and $d_{impactor}$ is the nozzle diameter.

As the fluid stream impacts the sample substrate 18, particulates generally within a designed-for size range are trapped on the surface of the substrate material and the fluid stream is drawn back towards the impactor 30 through a fourth fluid passageway 54 to the coupling arrangement 34 and onto the pump 16. Thus, the airflow is reversed after the impaction point and is pulled out the top of the collector 14. The air may be exhausted outside the housing 12 at some distance from the inlet opening 40 so as not to re-introduce previously sampled air back into the collector 20.

As will be seen in greater detail below, the reversal of the airflow after impaction allows the collector 14 to remain generally above and avoid significant interference with the sample substrate 18 which enables the sample substrate 18 to be easily advanced, changed out, replaced or otherwise adjusted. The positioning of the collector 14 over the sample substrate 18 and the corresponding reversal of airflow direction after impaction further allows the collector 14 to be integrated into an automated sample collection system as will be described in greater detail herein.

As an example, the impactor 30 may have a footprint of approximately 2 inches by 2 inches and a height of approximately 3 inches. However, the impactor 30 may comprise other suitable impaction size arrangements. Moreover, the impactor 30 may be implemented as a virtual impactor, cascade impactor or other suitable configuration, depending upon the specific sampling requirements.

The pre-impactor 28 is optional, but may be utilized for example, where it is desirable to filter particles that exceed a predetermined size requirement from the fluid stream. Filtering large particulates may be desirable for example, where the trigger device 10 is monitoring particulates that fall within a size range that can be inhaled. The pre-impactor 28 may be implemented using alternative particle size filtering techniques and may be implemented as an impactor, e.g., a virtual impactor.

Figure 5:
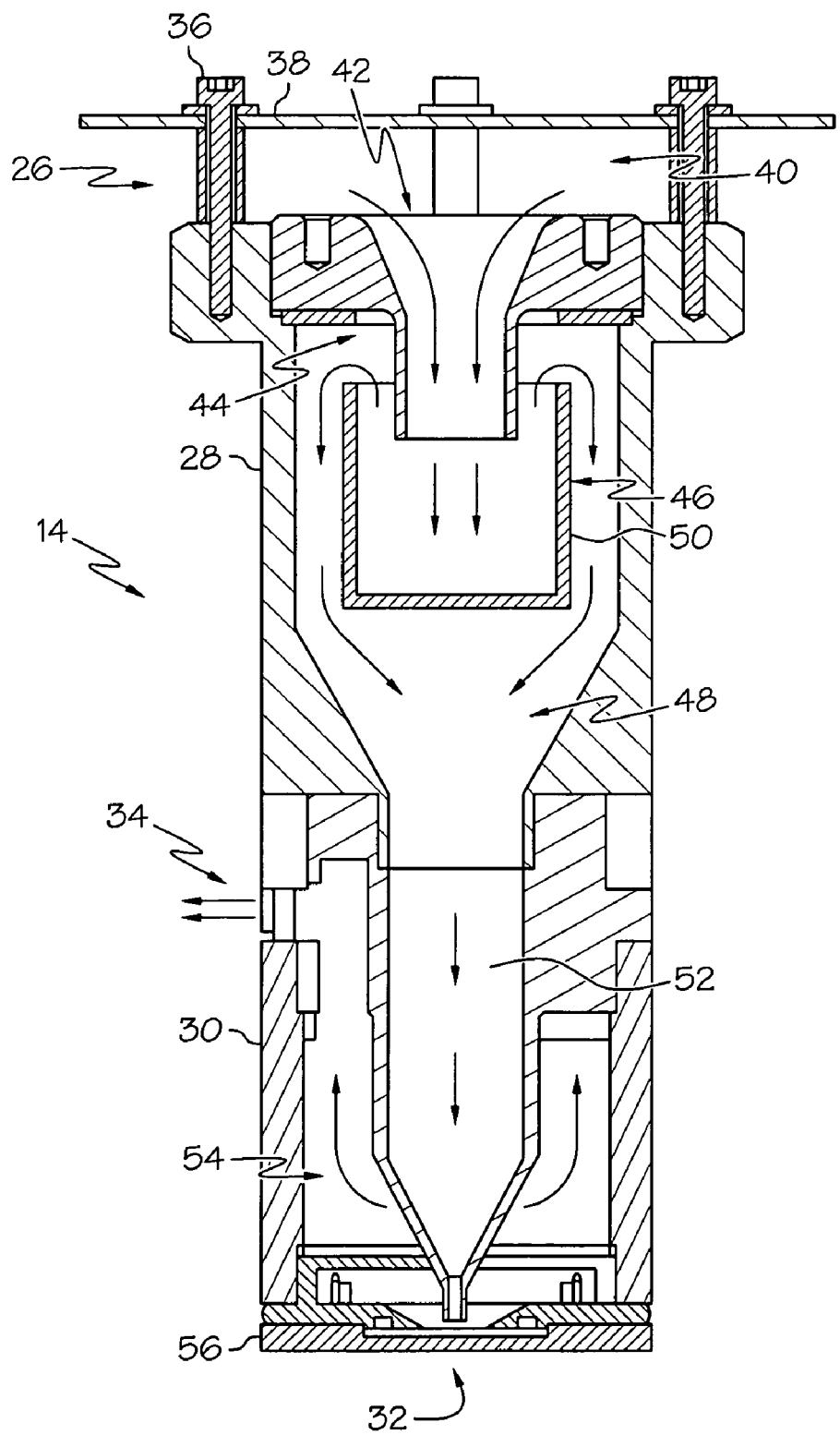
FIG. 5 is a cross sectional view of the collector of FIG. 2 taken along line 5-5 shown in FIG. 3.

With reference to FIGS. 1 and 5 generally, the inside diameter of the nozzle 32 of the collector 30, the distance between the nozzle 32 and the sample substrate 18 and the flow rate of the fluid stream drawn by the pump 16 define parameters that affect the size range of particles that are collected on the sample substrate 18. As such, depending upon the intended application, any one or more of the above-identified parameters may be made variable to provide a range of control to the particulate sizes captured on the sample substrate 18. Additionally, the flow rate of the collector 14 may use the nozzle 32 diameter as a critical orifice. That is, the flow rate may be controlled by the nozzle 32 diameter, e.g., if a proper vacuum is maintained through the collector 14.

Figure 2:
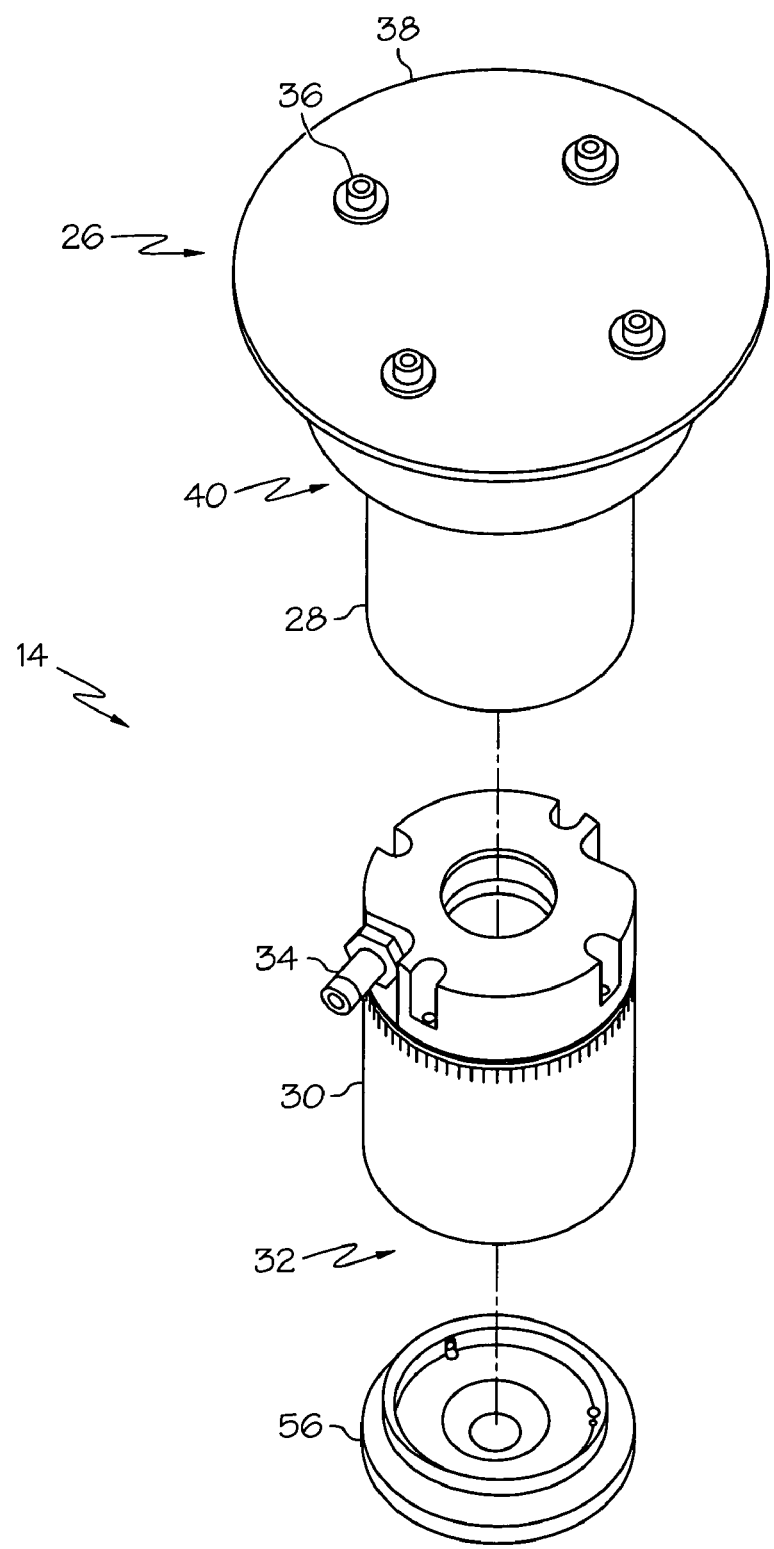
FIG. 2 is an assembly illustration of an exemplary collector according to an embodiment of the present invention.
Figure 3:
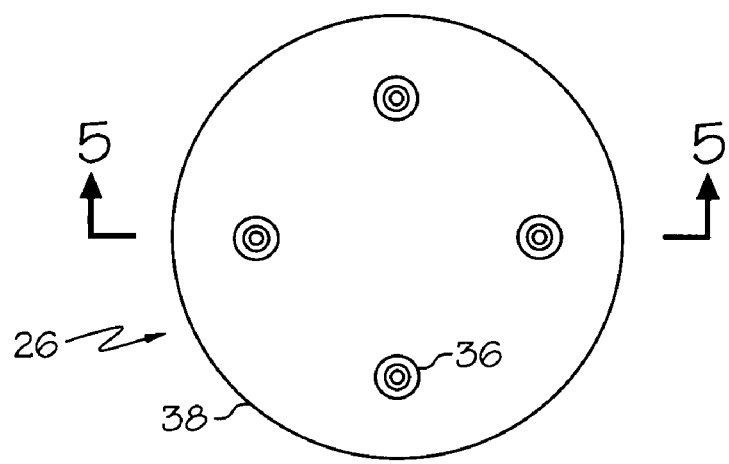
FIG. 3 is a top view of the collector of FIG. 2.
Figure 4:
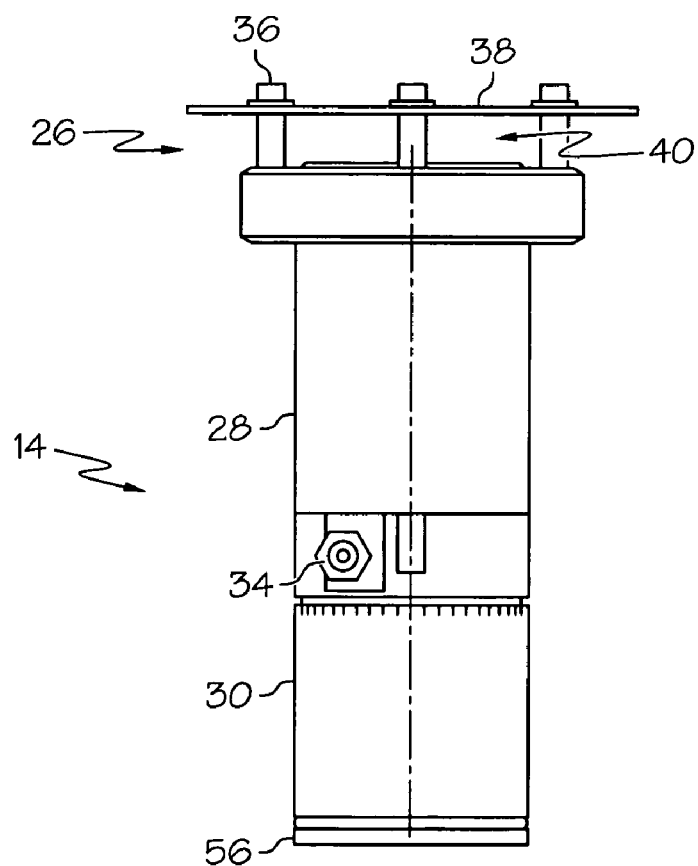
FIG. 4 is a side view of the collector of FIG. 2.

Referring to FIGS. 2, 4 and 5, the collector 14 may also include an optional end cap 56. The end cap 56 is positioned adjacent to the nozzle 32 and may screw onto or otherwise couple to the impactor 30 using any suitable arrangement. The end cap 56 may be provided to set the distance between the sample substrate 18 and the nozzle 32, which, as noted above, defines a parameter that affects the range of particulate sizes that are collected onto the sample substrate 18. As such, the end cap 56 may optionally be made adjustable so as to variably set the nozzle 32 to sample substrate 18 distance, e.g., as a rotatable graduated cylinder that threads up and down relative to the impactor 30.

Certain biological and/or chemical particles require only relatively low concentration numbers to result in undesirable environmental conditions. As such, an application that detects such biological or chemical particles may require that the trigger device 10 is capable of detecting trace levels of airborne biological or chemical agents. As will be described in greater detail below, one method of detecting particulates of interest is using an optical sensing arrangement. However, optical devices are sensitive to noise and interference from ambient light that could otherwise decrease the sensitivity of the detection and interrogation arrangement. As such, the impacting device may further include features that allow light tight cooperation between the collector 14 and the read head. For example, the end cap 56 may also assist in providing a light tight arrangement at least between the sample collection area of the sample substrate 18 and the collector 14.

Figure 6:
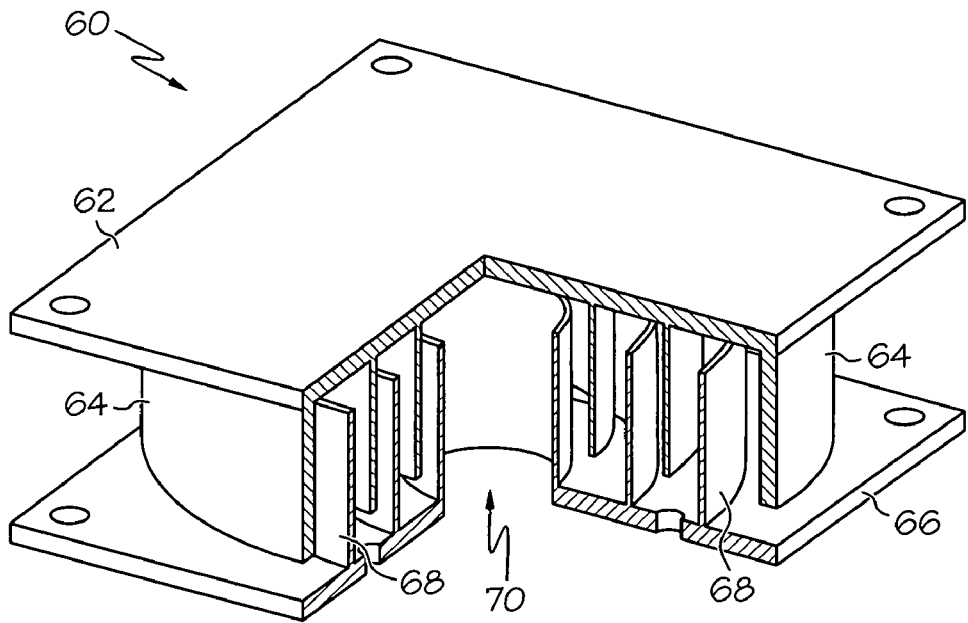
FIG. 6 is an illustration of a serpentine baffled intake manifold that may be used with the collector of FIGS. 2-5.

Referring to FIG. 6, one optional arrangement for decreasing noise due to ambient light is to provide a baffled intake manifold 60 incorporated with or in place of the inlet 26. As illustrated, the intake manifold 60 comprises a top section 62 having a plurality of downward extending baffles 64, a bottom section 66 having a plurality of upward extending baffles 68 and an output port 70 located in the central portion of the manifold 60 that cooperates with the first fluid passageway 42 when installed as part of the inlet 26. The upward and downward extending baffles 64 are offset so as to form a staggered arrangement, i.e., a labyrinth seal that prevents ambient light from penetrating to the manifold output port 70. Air is drawn from around the perimeter of the manifold 60 and flows through the labyrinth of upward and downward extending baffles 64 to the manifold 60 output. The fluid stream is capable of navigating the labyrinth. However, the ambient light is at least substantially blocked from penetrating to the manifold 60 output port 70. Moreover, the upward and downward extending baffles 64 may be painted black and other light absorbing treatments may be implemented.

In one exemplary application, the detection system is configured to sample the air for pathogens, allergens, bacteria, viruses, fungi, biological agents chemical agents and/or other viable microorganisms that fall within a range of sizes that can be inhaled. As such, the collector 14 may be designed to collect and deposit particulates generally within the size range of 1 μm to 10 μm on the sample substrate 18. The pump 16 may be implemented using a Gast Model SAA-V108-NQ oilless rocking piston vacuum pump, which is operable such that a the fluid stream travels at a flow rate of approximately 18.5 liters per minute (LPM) through the collector 14 and through the nozzle 32, which had an inner diameter of approximately 1.5 mm, to deposit a sample on the sample substrate 18 that may be approximately less than 2 mm in diameter. However, the specific application will determine the necessary flow rate, nozzle diameter, range of desired particulates and sample area. For example, it may be desirable to utilize a flow rate in the range of approximately 1-100 liters per minute.

Depending upon the specific application, alternative technologies may be used to collect and deposit samples on the sample substrate 18, including for example, electrostatic precipitation and cyclone devices.

The Sample Substrate

Figure 7:
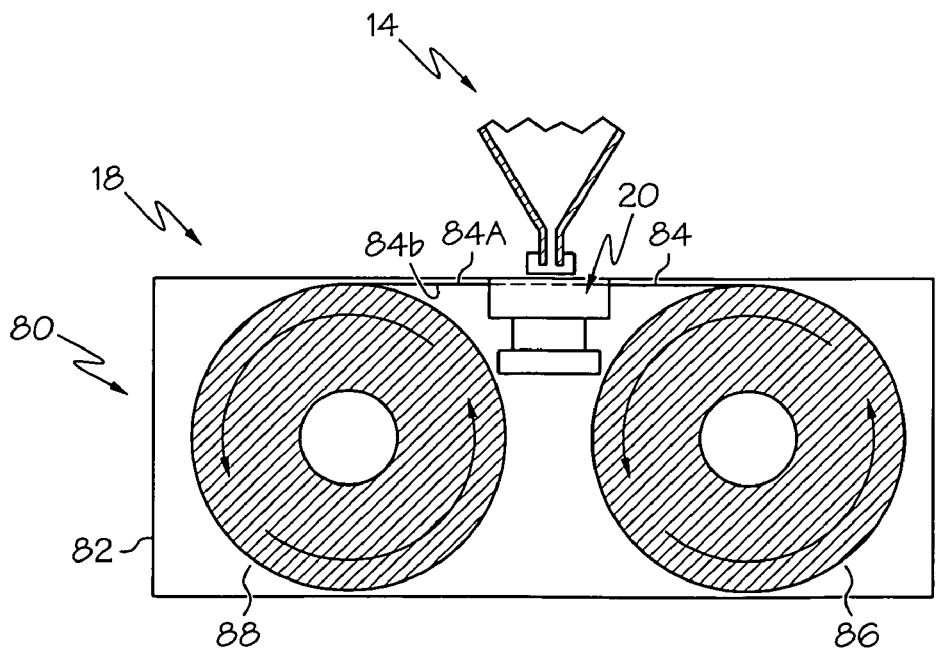
FIG. 7 is a schematic illustration of the sample substrate implemented on a cassette tape according to an embodiment of the present invention.

Referring to FIG. 7, the sample substrate 18 may be implemented as a tape system 80 that includes a housing, e.g., a tape cartridge 82, a length of tape 84 supported between spaced apart first and second drums 86, 88, e.g., in a manner similar to that of a cassette tape. The tape 84 may be controllably advanced, e.g., by a tape mechanism under the control of the processor 22 or other suitable control logic, such that the tape 84 is periodically advanced to a new sample area. The tape cartridge 82 is oriented on either side of the read head 20 such that a portion of the tape 84 is spooled out over the read head 20 and under the collector 14 as schematically illustrated.

The tape substrate is initially wound about the first drum 86. However, during operation, the tape 84 is indexed or otherwise advanced onto the second drum 88 after each sample is collected. The tape indexing or advancement may be controlled by the system to enable autonomous and continuous operation. For example, the tape system 80 may be configured to index, step or otherwise advance the tape 84 from the first drum 86 to the second drum 88 at a predetermined interval, such as every several minutes or whenever a suitable sample has been built up onto the tape 84. Alternatively, the tape may run continuously, e.g., where a suitable sample density can be built up on the tape substrate as the tape advances. Some sample buildup may dwell for a relatively long period in clean air and some samples may advance more rapidly if the air is particularly heavy with particulates. As such, the rate at which the tape 84 advances may be both application and operation/environmentally specific.

The tape substrate should be substantially transparent to ultraviolet light when used in conjunction with an optical read head 20 that uses fluorescence for particulate interrogation, as will be described in greater detail below. For example, the tape 84 may comprise a polymer such as a fluorinated ethylene copolymer (FEP) substrate. FEP as the tape substrate material provides low fluorescence background, high strength to thickness ratio, excellent transmission of the illumination source to the sample and is cost-effective for long periods of operation, e.g., approaching 1 year continuously. Alternatively, the tape 84 may comprise a fused silica ribbon as the tape substrate.

The tape 84 may have no applied coatings such as those typically used to trap and collect particulates. As such, a dry collection process is implemented by the collector 14 and sample substrate 18. Thus, no liquids or additional treatments or processing is required to collect and interrogate the sample. However, the tape 84 may be processed, e.g., plasma processed in a manner that makes a first surface 84A of the tape 84, i.e., the sample side, which is oriented proximate to the collector 14, sticky to aerosolized particles if required by a specific sampling application. Moreover, the plasma process does not significantly increase auto-fluorescence of the substrate. Thus, weak signals are not blocked from interrogation by the tape substrate itself. Plasma treatment of the tape 84 may be accomplished for example, by processing the FEP material in a Harrick Model PDC-32G 100Watt Argon Plasma chamber under vacuum for 60 minutes to treat the sample side of the tape 84.

The tape backside, i.e., the second surface 84B of the tape 84, which is positioned proximate to the read head 20, has low friction to promote efficiency of tape winding and interfacing with the read head 20. The backside of the tape 84 further functions to cover the previously collected samples on the sample side of the tape 84 as the tape 84 wraps on the second drum 88 of the tape cartridge 82. The tape cartridge 82 may be configured to shield the tape 84 except in the area of impaction corresponding to the sample collection area. The optional mask 24 may also provide impaction shielding as noted in greater detail herein.

According to one illustrative example, the dimensions of the tape are approximately 3.0 mm wide by approximately 0.03 mm thick. Further, the size of the first and second drums 88 may be approximately 2 to 4 inches in diameter. The use of a thin, flexible polymer tape 84 for the sample substrate 18 allows the tape cartridge 82 to be implemented in a relatively compact design. Moreover, the thin tape 84 enables spooling on the first and second drums 88, and allows a relatively long mean operation time for each tape cartridge 82. However, the duration of operation, i.e., the mean time between maintenance, and the sample interval will determine the drum size, tape dimensions and tape length used by the system.

The tape 84 can serve as a forensics record. As such, a time stamp and other relevant information may be associated with samples stored on the tape 84 that allows a forensics user to spin the tape 84 to a position of interest based upon a key that is electronically generated to identify the position of the samples and/or the time or other relevant data regarding when or how the samples were recorded. For example, forensics information may be generated by an analytical method such as polymerase chain reaction (PCR) analysis of the particles contained on the tape substrate. The location of the particles on the spooled tape may be tracked for example, by the number of increments the mechanical indexing system has provided in a given period of operation. A computer log of the indexes or step increments of the physical tape motion may then be utilized to determine the time base for a given location. Accordingly, under this arrangement, measuring the length of the tape corresponds to measuring the time stamp.

The Read Head

Figure 8:
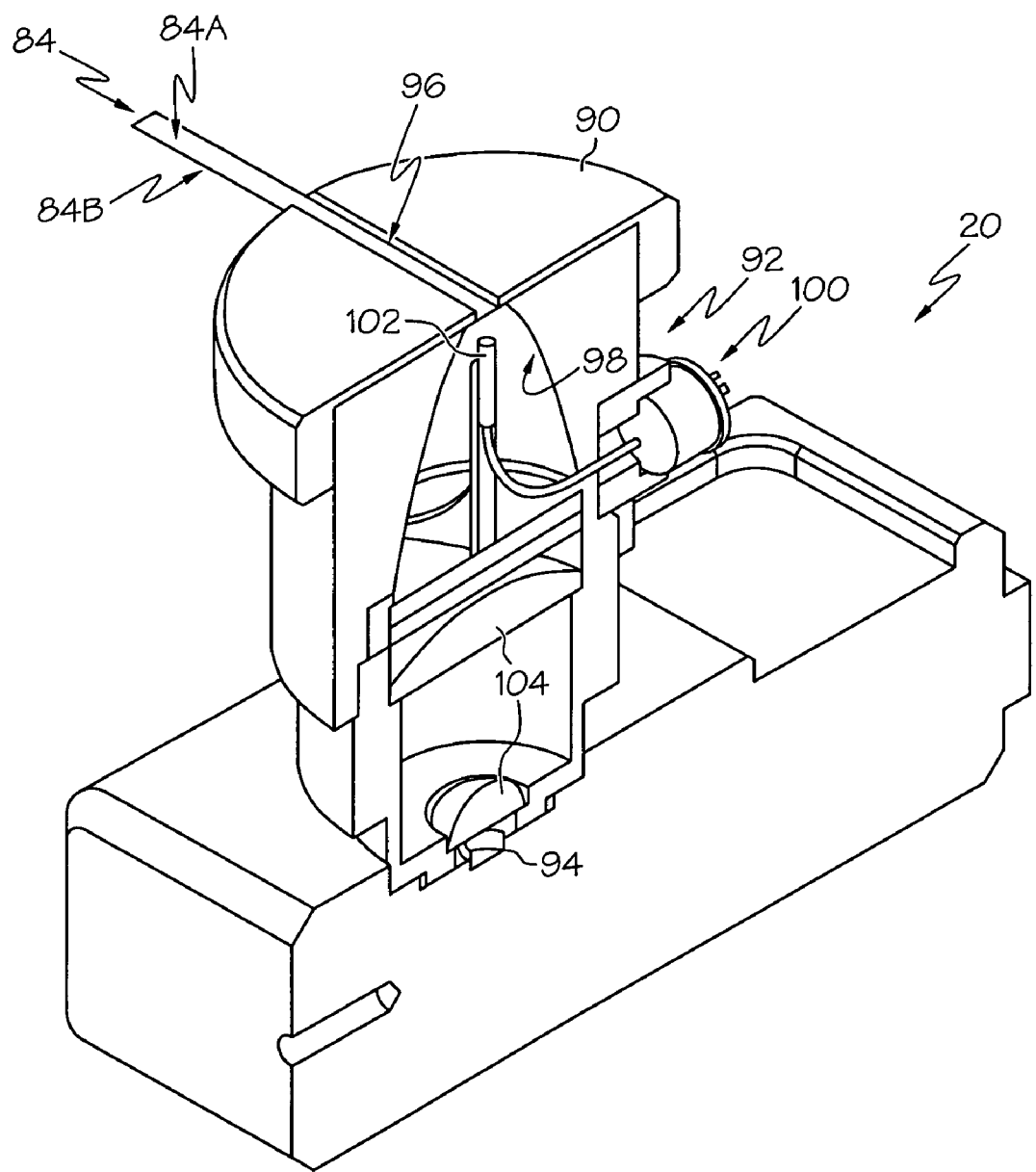
FIG. 8 is a cut out view of the read head.

With reference to FIG. 8, an optical read head 20 comprises a read head housing having a sample substrate receiving surface 90, an optical system 92 and a detector 94. The read head 20 may interrogate the sample as it is being collected and is positioned beneath the area of impaction on the sample substrate 18 corresponding to the sample collection area, e.g., between the first and second drums 86, 88 of the tape cartridge 82. A channel 96 passes through the sample substrate receiving surface 90 for receiving the tape 84 there through. The channel 96 aligns the tape 84 with the optical system 92 for interrogating the sample and mitigates defocus issues thus eliminating a source of noise in the sample data.

The optical system 92 comprises a generally concave reflection surface 98, a radiation source, e.g., an illuminator 100, positioned to one side of the read head 20, a fiber optic element 102 and one or more lenses and/or filters 104. The illuminator 100 comprises a narrowband radiation source such as a 280 nm ultraviolet light emitting diode or other suitable narrowband radiation source that is configured to emit energy at a wavelength that is appropriate for stimulation of fluorescence or for detection of aerosolized particulates of interest. The fiber optic element 102 directs the radiation source output energy from the side of the read head 20 towards the portion of the tape 84 that contains the current sample. The rear of the reflection surface 98 acts as a registration plane for the tape channel 96 and thus further serves to register the tape 84 directly adjacent to optical system 92, which self-aligns the sample region with the target interrogation zone of the optical system 92, and thus improves ruggedness of the system by reducing focus variability.

While other arrangements may be used, such as a turning prism or other optical element, the fiber optic element 102 may minimize obscuration of the signal light emitted from the sample as well as the reflected light from the reflection surface 98 towards the detector 94, thus enabling efficient delivery of the radiation source to the sample area, and collection of the signal light emitted or reflected towards the detector 94. Energy is reflected back from the reflection surface 98 and is filtered and focused onto the detector 94 by one or more lenses 104, which may include collimating lenses, optical filters and other necessary filtering and focusing devices. The detector 94 comprises for example, a low noise DC silicon photodiode with femtoWatt sensitivity.

The reflection surface 98 may comprise a parabolic mirror where increased sensitivity is required, as parabolic mirrors offer a large light capturing ability and also do not suffer from spherical aberration. As such, relatively weak or faint signals that may otherwise be lost due to optical aberrations can be detected. For example, the high efficiency of the parabolic mirror may capture approximately up to 89% of the emitted light from the illumination source. The high optical efficiency also delivers a high signal to noise ratio, which leads to high confidence levels and low false positive and false negative rates.

One method for characterizing individual airborne biological and/or chemical particles in substantially real-time is by measuring radiation-induced auto-fluorescence of such particulates. Particulates including biological or chemical components absorb light at a particular frequency and emit fluorescence at another particular frequency. For each such particulate, the emitted fluorescence frequency is dependent on the absorption frequency. However, the absorbed frequency and the emitted fluorescence frequency are different for different types of biological or chemical components. Thus, biological or chemical particulates may be characterized by a "fingerprint" which is defined by their fluorescence frequency.

The tape 84 provides a low fluorescence background suitable to enable the optical read head 20 to interrogate the sample. The parabolic mirror collects and collimates the fluorescence signal, and the collimated signal is filtered to block the LED or other radiation source illumination. Further, condenser optics 104 focus the signal energy onto the detector 94, e.g., a 1 mm diameter detector, at the base of the optical read head 20. In one exemplary application, the particles of interest fluoresce under UV illumination and generate light in a longer wavelength region than that of the LED, e.g., 320-450 nm or more, which is detected by the detector 94. The processor 22, which is illustrated in FIG. 1, analyzes the detector output signal for fluorescence information and determines whether an action event is required by identifying fingerprints or other suitable identifying criteria of the particulates of interest.

Figure 9:
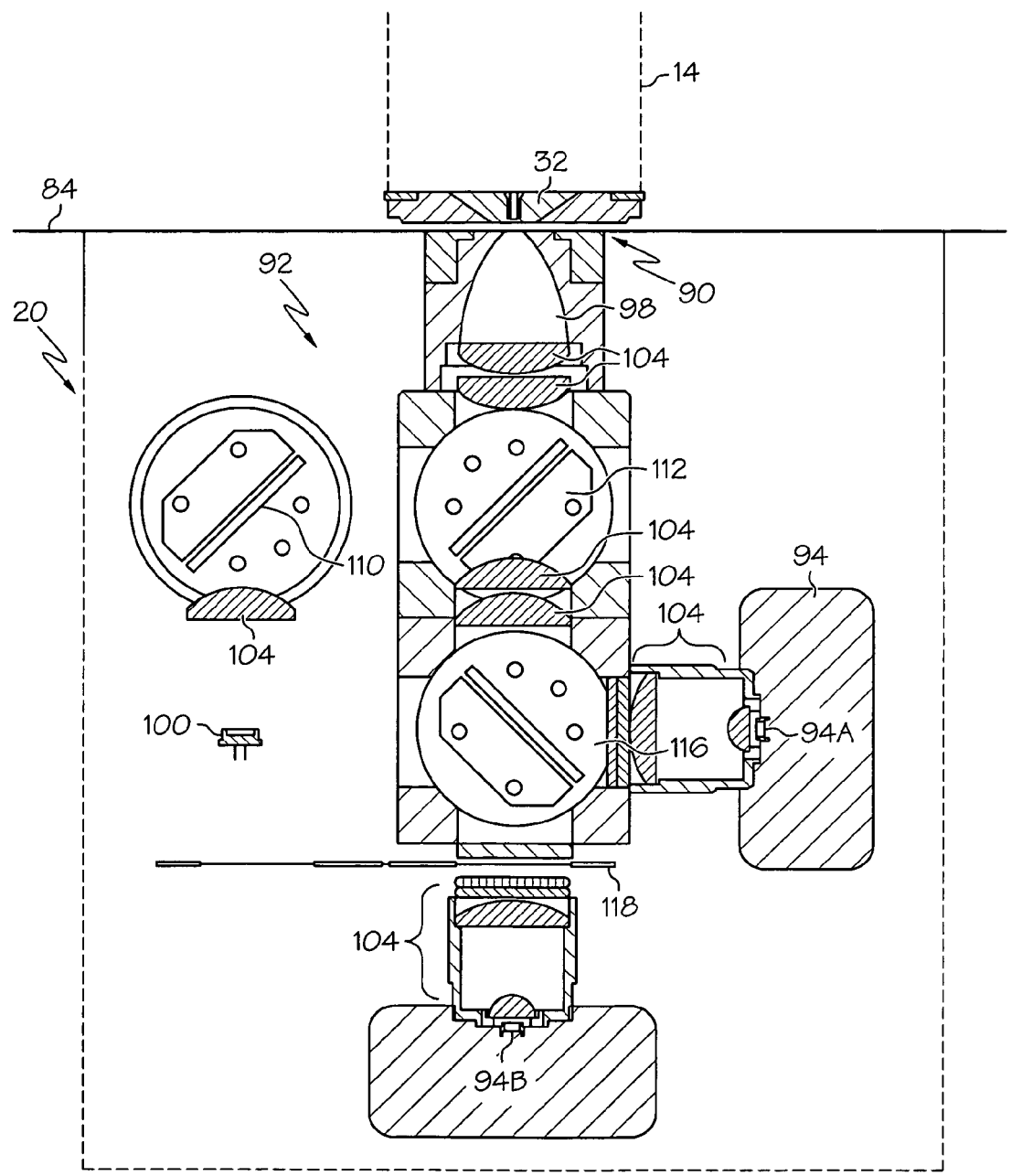
FIG. 9 is a cut out view of an alternative read head.

With reference to FIG. 9, an alternative optical system for the read head 20 is illustrated. In this regard, the read head 20 shown in FIG. 9 includes a read head housing having a sample substrate receiving surface 90 including a channel 96 that passes through the sample substrate receiving surface 90 for receiving the tape 84 there through in a manner analogous to that described with reference to the read head 20 illustrated in FIG. 8. Also the read head 20 may interrogate the sample as it is being collected and is positioned generally beneath the area of impaction on the sample substrate 18 corresponding to the sample collection area, e.g., between the first and second drums 86, 88 of the tape cartridge 82 in a manner analogous to that described with reference to the read head 20 illustrated in FIG. 8.

As shown in FIG. 9, the read head includes a plurality of detectors 94, e.g., two detectors 94A, 94B. Each detector 94A, 94B monitors radiation that has been filtered into a predetermined spectral range. For example, detector 94A may comprise a UV channel detector and the second detector 94B may comprise a visible or near visible spectrometer channel detector. The two detectors 94A, 94B monitor the fluorescence of the impacted sample on the tape substrate.

A radiation source 100 emits a beam that is directed towards a reflection surface 98, such as a parabolic mirror. For example UV illumination from an LED 100, e.g., an SUVOS 280 nm LED is collimated, filtered and directed, e.g., by lens 104, a first dichroic element 110 and a second dichroic element 112, towards the reflection surface 98. Further, the first dichroic element 110 and the second dichroic element 112 may subtract a range of wavelengths such as the 300-400 nm emission tail from the illumination radiation. The lenses 104 at the entrance of the reflection surface 98 focus the illumination radiation to a relatively small spot, e.g., approximately a 600 micron spot, on the tape substrate 18 within the sample collection area. Impacted particles from the collector nozzle fluoresce and their emission is captured by the high numerical aperture parabolic mirror, which collimates the emission and directs this energy back through the optical system 92 to the UV channel detector 94A and the visible spectrometer channel detector 94B.

In this exemplary configuration, the UV channel detector 94A looks at emission in a first spectral range, e.g., 305-380 nm region. The visible spectrometer channel detector 94B looks at energy in a second spectral range, e.g., in the 400-570 nm region. The visible spectrometer channel detector 94B also includes a continuous narrowband filter that divides the visible emission into a plurality of ranges, i.e., bins, e.g., 10-nm bins across at least a portion of the second spectral range. A chopper wheel 118 under the filter 104 may be used to rotate a slit across this spectrum and thus sample the spectral data, or to remain in a fully open position, allowing the entire spectrum to transmit to the detector 94B. For example, variable slit sizes may be provided on the chopper wheel 118 to achieve different sampling goals.

According to one aspect of the present invention, the read head of FIG. 9 may be operated in one of two modes. In a first exemplary mode, the read head captures radiation within the visible and/or near visible spectrum simultaneously with the radiation within the UV spectrum while monitoring for positive events, e.g., data indicative of biological or chemical particulates of interest. The system will likely operate in this mode for the greatest percentage of its operational life, since most of the time the read head is reading negative events. A second exemplary mode takes place when a possible "positive" event occurs. In the second mode, the chopper 118 is engaged to scan the corresponding spectrum (e.g., UV-VIS spectrum depending upon the filter element used) and record a spectral signature. This approach allows the system to conserve diode life by being able to switch modes of operation on the LED 100 from a short pulse monitoring status, to a continuous DC mode while the chopper scans the spectrum.

Figure 10:
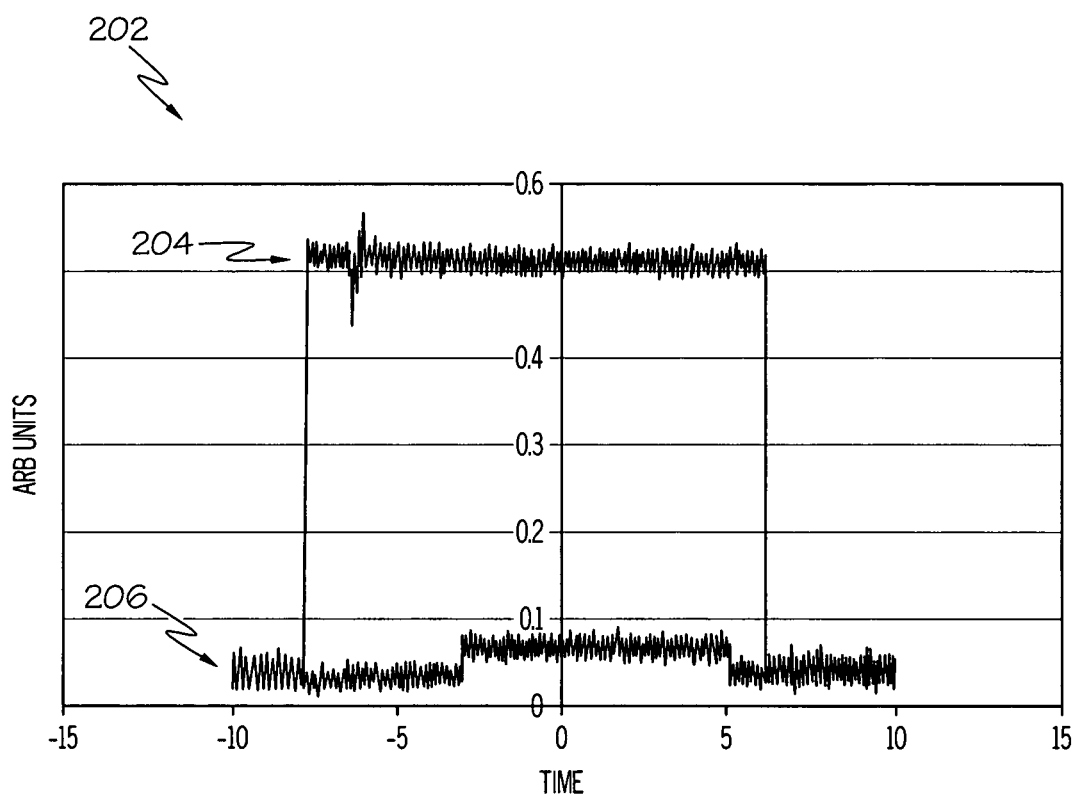
FIG. 10 is a chart constructed from exemplary output data from the read head of FIG. 8 comparing a signal of interest and a background signal.

With reference to FIG. 10, a chart 202 illustrates an exemplary response plot of a signal of interest 204 compared to a background signal 206, such as from data measured from the output of the detector 94. The exemplary signal of interest 204 in the chart 202 represents a detection of 1 micron *Bacillus globigii* (Bg) particulates at 1000 colony forming units (CFU) per liter of air collected over a 5 minute collection period operating a collector at 181 pm. As the chart 202 illustrates, the signal of interest 204 (BG) has a greater signal level than the background signal 206.

According to one exemplary implementation of the present invention, as the particles build up in the current sample area of the tape 84, the read head 20 interrogates the sample for particulates of interest. As such, the system may detect particulates of interest in real time, or at least substantially real time. That is, the sample is interrogated while it is being accumulated on the sample substrate 18. Such an approach may result in faster response time, may avoid missing data, and provides more time for the processor 22 to make decisions. After a predetermined period, the tape 84 is advanced and a new sample is collected and interrogated. The above process repeats until the available tape 84 is exhausted, upon which time, a new tape 84 can be loaded into the system.

The impaction and collection system may be integrated with the read head 20 so as to exhibit "light tight" system performance. That is, the collector 14 does not allow unwanted or excessive ambient light to pass through to the sample collection area (read zone) on the tape 84 where unwanted background light could blind or otherwise diminish the sensitivity of the optical detection system. Thus, the trigger device 10 is suitable for use in indoor and lighted conditions without resort to optical filters to reduce the noise introduced by ambient light.

The implementation of the sample substrate 18 as a replaceable tape cartridge 82 allows the tape cartridge 82 to be pulled out and input into an "identifier" system. For example, if the trigger sounds an alarm on a sample, it may be desirable to advance the tape 84 to another station within the system (not shown), or to a separate device, that can identify the particulates that triggered the alarm. In this regard, the sample that triggers the alarm may be sequestered or otherwise advanced to a predetermined location on the tape substrate within the tape cartridge 82 for identification.

Still further, air monitoring may provide a historical characterization of the of aerosol exposure and in the linkage of the levels of aerosol particles and their toxic constituents to their sources.

Operation of the Trigger Device

Figure 11:
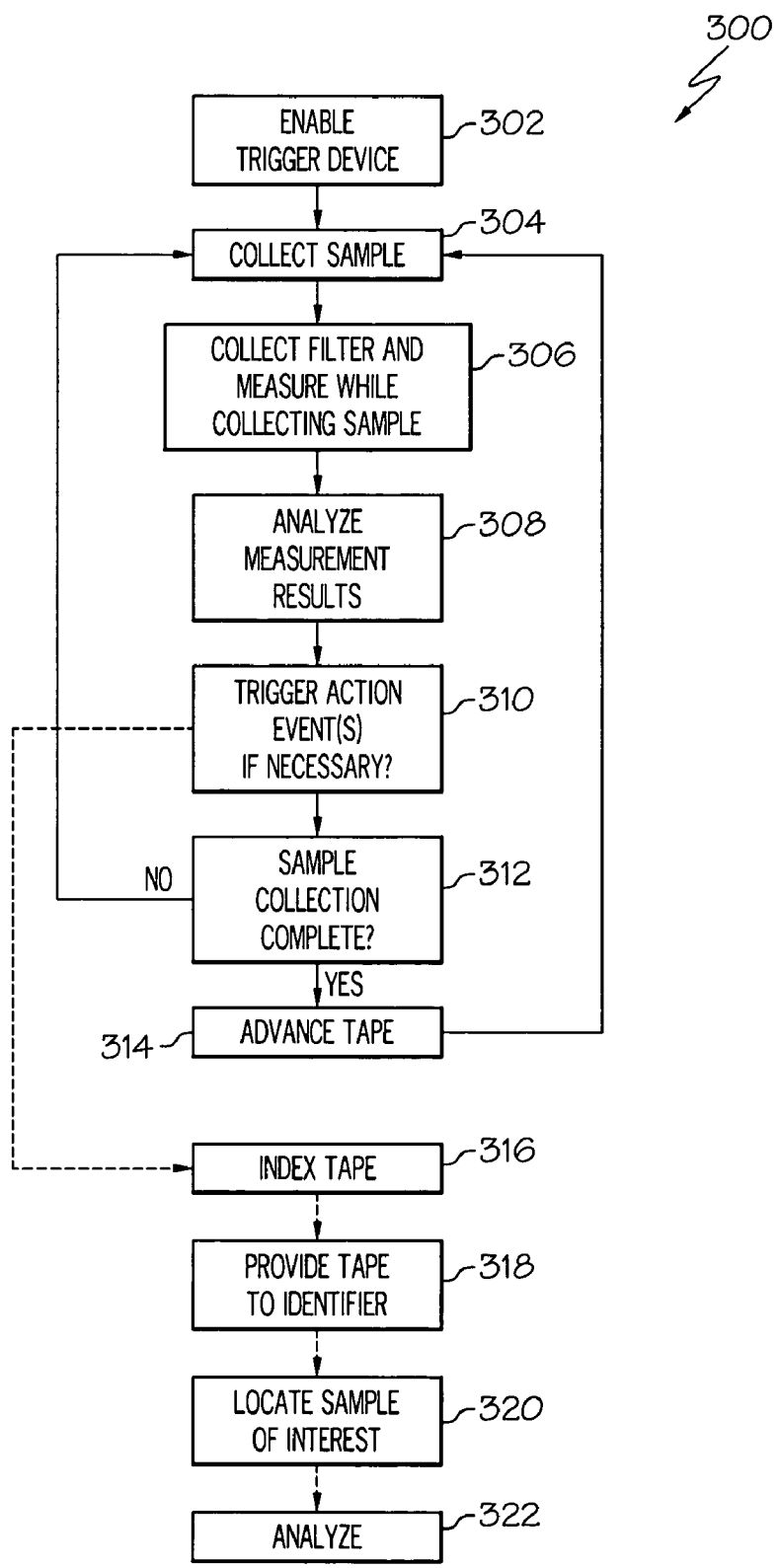
FIG. 11 is a flow chart illustrating a method of detecting particulates of interest using the trigger device.

A method 300 of operating the trigger device 10 is illustrated with reference to FIG. 11. Initially, the trigger device 10 is turned on or is otherwise enabled at 302. During operation, the collector 14 is operated to collect and impact a sample of particulates, e.g., falling within a predetermined size range at 304. For example, the collector 14 may be operated at a flow rate in the range of approximately 1-100 liters of air per minute to collect and impact particulates onto the tape sample substrate 18 in a localized sample area that is approximately 1 millimeter in diameter. The rest of the tape 84 is shielded or masked off from the impaction area during the sampling operation so as to not contaminate adjacent sample areas.

The read head 20 may be constantly on during the sample collection process, thus the sample is interrogated while being collected. This allows the system to monitor the build up of signal during the collection period and thus manage the time of monitoring effectively. Thus, the system is reading while collecting, i.e. there are no intermittent cycles that would otherwise delay or prolong the detection of particulates of interest. As such, the present invention can yield information about the rate that a threat builds up.

Fluorescence or other suitable interrogation data from the impacted particles is collected, filtered and measured at 306, e.g., using one or more detectors as set out in greater detail herein. An algorithm checks the measurement results to determine whether an action event should be triggered at 308. In one illustrative example, an algorithm uses slope and threshold information to determine if an event has occurred with sufficient confidence to generate an alarm and send a signal. The system may also monitor trends that do not trigger an alarm. However, fluctuations in particle detection that cause sharp changes in the slope of the collected data may define alarm triggering events at 310.

For example, an alarm triggering event may be determined at 310 where a significant change is detected in the signal strength which has risen beyond the statistical background of negative events. Alternatively, the rate of increase, linearity of increase, amplitude of the increase in a given time period, e.g., less than 1 minute, may also be considered alone or in combination.

Next, the sample collection cycle is queried at 312. If the sample collection cycle has not completed, the process continues to interrogate and analyze the sample area by looping back to 304. If the sample cycle is complete, then the tape 84 indexes to a clean substrate region at to get rid of the background material at 314 and the process loops back to the sample collecting portion of the cycle at 204. Thus, the system operates continuously and autonomously. The period at which the tape 84 advances may depend upon a number of operational and/or environmental factors such as the rate of particulate buildup, a programmed rate of tape advancement, etc.

If it is necessary to trigger an action event at 310, the appropriate action is taken. This may comprise logging information into a historical file, sending a communication, sounding an alarm, etc. It may also be desirable to attempt to more precisely identify the particulates of interest. As an optional process, if a positive event occurs, the tape may be indexed to a predetermined location at 316. For example, the tape may be jogged forward so that the current sample that triggered the action event is covered and protected. The tape may then be provided to an identifier at 318. The identifier may be incorporated with the trigger device, or the tape may be removed from the trigger device and may be physically relocated to a separate identification device. The identification device locates the sample at 320 and the sample is further analyzed at 322.

Having described the invention in detail and by reference to preferred embodiments thereof, it will be apparent that modifications and variations are possible without departing from the scope of the invention defined in the appended claims.

What is claimed is:

1. A trigger device for detecting particulates of interest comprising:
- a collector configured to deposit samples of particulates within a sample collection area onto a sample substrate;
- a read head positioned proximate to said sample collection area generally opposite of said collector such that said sample collection area is between said collector and said read head, said read head comprising a housing, an optical system and at least one detector, and
- a processor operatively configured to analyze a signal from said at least one detector and to trigger an event if particulates of interest are detected in said sample area, wherein:
- said read head housing comprises a sample substrate receiving surface including a channel for receiving said sample substrate;
- said read head optical system comprises:
  - a concave reflection surface having a back surface positioned adjacent to said channel so as to register said sample substrate when received in said channel adjacent to said optical system of said read head; and
  - an illumination source that illuminates at least a portion of said sample area, wherein radiation emitted by said illumination source is directed towards said reflection surface;
- said at least one detector collects radiation within said read head including at least one of light reflected from said reflection surface and radiation which may be emitted by samples collected within said sample area; and
- said sample substrate is oriented generally between said collector and said read head, said sample substrate configured to collect samples deposited in said sample area on a first side of said sample substrate proximate said collector for interrogation of collected samples by said read head through a second, opposite side of said sample substrate which is aligned with said optical system of said read head.

2. The trigger device according to claim 1, wherein said collector and said optical read head are each configured with respect to said sample substrate so as to form a light tight relationship therebetween.

3. The trigger device according to claim 1, wherein said collector comprises a baffled intake manifold so as to block ambient light from entering said sample area via said collector.

4. The trigger device according to claim 1, wherein said collector comprises a nozzle from which a fluid stream is ejected from said collector towards said sample area, wherein a flow rate of said stream is controlled by a size of said nozzle.

5. The trigger device according to claim 1, wherein said collector ejects a fluid stream towards said sample area, and said stream is reversed and drawn back out through said collector.

6. The trigger device according to claim 1, wherein said collector comprises an end cap that is adjustable to set the space between a nozzle of said collector and said collection area.

7. The trigger device according to claim 1, wherein said sample substrate comprises a tape that passes through said channel in said read head so as to register said sample area with said reflection surface.

8. The trigger device according to claim 1, wherein said sample substrate comprises a Fluorinated Ethylene Copolymer material (FEP).

9. The trigger device according to claim 1, further comprising a mask for limiting the dispersion of said sample on said sample substrate.

10. The trigger device according to claim 1, wherein said illumination source is configured to illuminate said sample substrate during sample collection by the collector so as to provide a substantially real-time response to the detection of at least one type of particulates of interest.

11. The trigger device according to claim 1, wherein said reflection surface comprises a parabolic mirror.

12. The trigger device according to claim 1, wherein said processor is operatively configured to activate an alarm based upon a detection of a fluorescence of a particle of interest.

13. The trigger device according to claim 1, wherein said processor is operatively configured to activate an alarm based upon a detection of a fluorescence that is not consistent with a previously determined trend.

14. A read head for a trigger device comprising:

a housing including a first surface having a channel therethrough for receiving a tape substrate;

an optical system comprising:

a concave reflection surface having a backside adjacent to at least a portion of said channel in said first surface so as to register said tape substrate adjacent to said optical system when said tape substrate is positioned within said channel;

a radiation source configured to emit a beam that is directed towards said reflection surface so as to illuminate a sample collected on a sample region of said tape substrate that is aligned with said backside of said reflection surface; and at least one filter arranged to filter at least one of radiation which has been reflected from said reflection surface or radiation which has been emitted from particulates collected on said tape substrate within said sample region that emit radiation through said backside of said reflection surface; and at least one detector arranged to receive said radiation filtered by said at least one filter and output a signal corresponding to the filtered radiation.

15. The read head according to claim 14, wherein said reflection surface comprises a parabolic mirror.

16. The read head according to claim 14, wherein said radiation source comprises an ultraviolet Light Emitting Diode.

17. The read head according to claim 14, wherein said radiation source beam is directed from a side of said housing towards said reflection surface by a fiber optic element.

18. The read head according to claim 14, wherein said at least one filter comprises a first condenser lens positioned adjacent to said detector and a second condenser lens spaced from said first condenser lens.

19. The read head according to claim 14, wherein said detector comprises a silicon photodiode detector.

20. A read head for a trigger device comprising:

a housing including a first surface having a channel therethrough for receiving a tape substrate;

an optical system comprising:

a concave reflection surface having a backside adjacent to at least a portion of said channel in said first surface so as to register said tape substrate adjacent to said optical system when said tape substrate is positioned within said channel;

a radiation source configured to emit a beam that is directed towards said reflection surface so as to illuminate a sample collected on a sample region of said tape substrate that is aligned with said backside of said reflection surface; and at least one optical device positioned to filter at least one of radiation which has been reflected from said reflection surface or radiation which has been emitted from particulates collected on said sample area of said tape substrate that emit radiation through said backside of said reflection surface, into at least a first spectral range and a second spectral range;

a first detector arranged to receive radiation that is filtered into said first spectral range and output a first signal corresponding to the filtered radiation in said first spectral range; and a second detector arranged to receive radiation that is filtered into said second spectral range that is different from said first spectral range and output a second signal corresponding to the filtered radiation in said second spectral range.

21. The read head according to claim 20, further comprising a first dichroic element and a second dichroic element that collimate and filter said beam before said beam reaches said reflection surface.

22. The read head according to claim 21, wherein said first and second dichroic elements subtract an emission tail of said beam before said beam reaches said reflection surface.

23. The read head according to claim 20, wherein said concave reflection surface comprises a parabolic mirror configured to collimate and direct radiation so as to be detected by said first and second detectors.

24. The read head according to claim 20, wherein said first detector is configured to detect energy generally within an ultraviolet light range and said second detector is configured to detect energy generally within a visible or near visible light range.

25. The read head according to claim 24, wherein said ultraviolet light range comprises at least a 300 to 380 nanometer region and said visible or near visible light range comprises at least a 400 to 570 nanometer region.

26. The read head according to claim 20, further comprising a narrow band filter that divides radiation detected by said second detector into a plurality of ranges.

27. The read head according to claim 26, wherein said narrow band filter divides radiation received by said second detector into a plurality of regions, where each region is a subset of a spectral range defined between approximately 300 and 570 nanometers.

28. The read head according to claim 26, wherein said narrow band filter comprises a chopper wheel having a plurality of slits therethrough.

29. A method of detecting a particulate of interest comprising:
   utilizing a collection device to collect a sample of particulates within a predetermined sample area onto a first side of a tape substrate during a collection period;
   utilizing a read head positioned proximate to said sample collection area generally opposite of said collector to illuminate said sample area through a second, opposite side of said tape substrate which is aligned with an optical system of said read head during at least a portion of said collection period by:
      directing a beam towards a concave reflection surface of said optical system that is oriented such that the rear of the reflection surface is registered with said sample area of said tape substrate that is adjacent to said optical system;
   collecting and filtering at least one of radiation which has been reflected from said reflection surface or radiation which has been emitted from particulates collected on the tape substrate that emit radiation through said reflection surface to generate illumination data;
   computing slope and threshold information from said data to determine if a positive event has occurred with sufficient confidence to generate an action event; and
   automatically indexing said tape to a clean substrate region after said collection period.

30. The method according to claim 29, wherein collecting a sample comprises impacting particulates onto said tape in a localized spot having a diameter smaller than approximately 2 millimeters.

31. The method according to claim 29, further comprising arranging said collection device and said read head so as to achieve a light tight optical system where said sample area is illuminated by said optical read head.

32. The method according to claim 29, further comprising:
   recording information associated with samples collected on said tape substrate;
   removing said tape from said read head;
   providing said tape in an identifier;
   locating a sample of interest based upon said information; and
   identifying particulates of interest.

33. The method according to claim 29, further comprising monitoring radiation in both an ultraviolet spectral range and in a visible or near visible spectral range to generate said data.

34. The method according to claim 33, further comprising:
   detecting a potential positive event;
   utilizing a narrow band filter to sample a plurality of spectral bands within said visible or near visible spectral range to generate a spectral signature; and;
   analyzing said spectral signature to determine whether to trigger said action event.

35. The method according to claim 29, wherein said providing a tape substrate comprises providing a Fluorinated Ethylene Copolymer material (FEP) material as said tape substrate.

* * * * *